United States Patent
Fang et al.

(10) Patent No.: US 8,295,929 B2
(45) Date of Patent: Oct. 23, 2012

(54) GLASS FEEDTHROUGH ASSEMBLIES FOR IMPLANTABLE MEDICAL DEVICES

(75) Inventors: Zhi Fang, Maple Grove, MN (US); Xingfu Chen, Lino Lakes, MN (US)

(73) Assignee: Medtronic, Inc., Minneapolis, MN (US)

(*) Notice: Subject to any disclaimer, the term of this patent is extended or adjusted under 35 U.S.C. 154(b) by 642 days.

(21) Appl. No.: 12/469,080

(22) Filed: May 20, 2009

(65) Prior Publication Data
US 2009/0292326 A1   Nov. 26, 2009

Related U.S. Application Data

(60) Provisional application No. 61/055,023, filed on May 21, 2008.

(51) Int. Cl.
*A61N 1/00* (2006.01)
(52) U.S. Cl. ............... 607/37; 607/36; 607/38
(58) Field of Classification Search ......... 607/36–38
See application file for complete search history.

(56) References Cited

U.S. PATENT DOCUMENTS

| | | | |
|---|---|---|---|
| 5,045,508 A | 9/1991 | Brow et al. | |
| 5,236,495 A | 8/1993 | Manabe et al. | |
| 5,262,364 A | 11/1993 | Brow et al. | |
| 5,830,480 A | 11/1998 | Ducheyne et al. | |
| 5,965,469 A | 10/1999 | Kilgo et al. | |
| 6,037,539 A | 3/2000 | Kilgo et al. | |
| 6,090,503 A | 7/2000 | Taylor et al. | |
| 7,022,198 B2 | 4/2006 | Bruce et al. | |
| 2003/0134194 A1 | 7/2003 | Lasater | |
| 2004/0191621 A1 | 9/2004 | Heller, Jr. | |
| 2005/0092507 A1* | 5/2005 | Marshall et al. | ........... 174/50.59 |
| 2006/0247714 A1* | 11/2006 | Taylor et al. | ................. 607/36 |

FOREIGN PATENT DOCUMENTS

WO    2006115837    11/2006

OTHER PUBLICATIONS

International Search Report, PCT/US2009/04470, 3 sheets, mailed Oct. 19, 2009.

* cited by examiner

*Primary Examiner* — Niketa Patel
*Assistant Examiner* — Mallika D Fairchild

(57) ABSTRACT

A feedthrough assembly of an implantable medical device includes a glass insulator containing at least approximately 20 mol % of calcium oxide (CaO), preferably of a CABAL-12 type composition. The assembly is either manufactured so that the glass insulator includes a surface layer including calcium phosphate, preferably of relatively low solubility, or is assembled in the implantable device so that the glass insulator is exposed to phosphate-containing body fluid, when the device is implanted, for the formation of a surface layer including calcium phosphate.

9 Claims, 6 Drawing Sheets

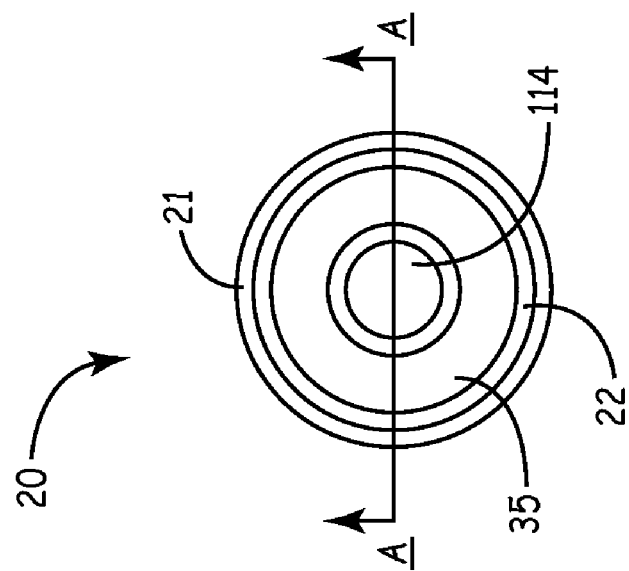
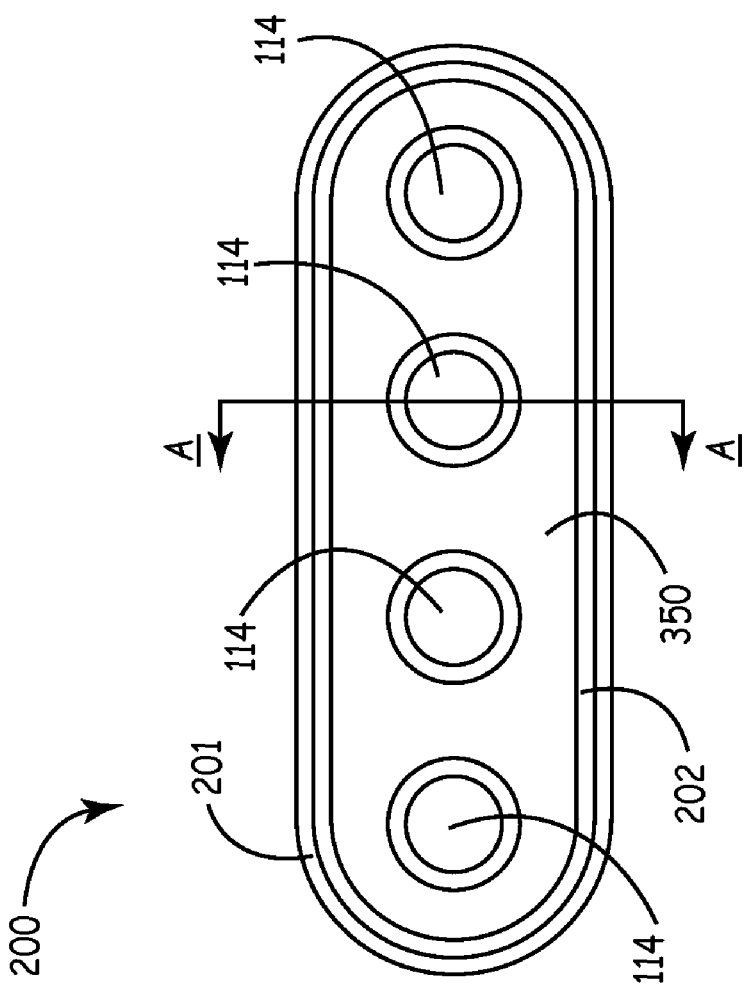

GLASS FEEDTHROUGH ASSEMBLIES FOR IMPLANTABLE MEDICAL DEVICES

CROSS REFERENCE TO RELATED APPLICATION

This application claims the benefit of U.S. Provisional Patent Application No. 61/055,023, filed May 21, 2008, the disclosure of which is incorporated by reference herein in its entirety.

FIELD

The present invention pertains to implantable medical devices and more particularly to glass feedthrough assemblies for the devices.

BACKGROUND

Implantable medical devices (IMD's), for example, cardiac pacemakers, defibrillators, neurostimulators and drug pumps, which include electronic circuitry and battery elements, require a housing to contain and hermetically seal these elements within a body of a patient. Many of these IMD's include one or more electrical feedthrough assemblies to provide electrical connection between the elements contained within the housing and components of the IMD external to the housing, for example, sensors and/or electrodes and/or lead wires mounted on an exterior surface of the housing, or electrical contacts housed within a connector module, which is mounted on the housing to provide coupling for one or more implantable leads, which typically carry one or more electrodes and/or one or more other types of physiological sensors. A physiological sensor, for example a pressure sensor, incorporated within a body of a lead may also require a hermetically sealed housing to contain electronic circuitry of the sensor, and, thus an electrical feedthrough assembly to provide electrical connection between one or more lead wires, that extend within the implantable lead body, and the contained circuitry.

A feedthrough assembly typically includes one or more feedthrough pins that extend from an interior to an exterior of the housing through a ferrule; each feedthrough pin is electrically isolated from the ferrule, and, in the case of the multipolar assembly, from one another, by an insulator element, for example, glass or ceramic, that is mounted within the ferrule and surrounds the feedthrough pin(s). Glass insulators are typically sealed directly to the pin(s) and to the ferrule, for example, by heating the assembly to a temperature at which the glass wets the pin(s) and ferrule, while ceramic insulators are typically sealed to the pin(s) and to the ferrule by a braze joint.

Special glass compositions, which are suitable for use as insulators in implantable feedthrough assemblies are disclosed in commonly-assigned U.S. Pat. No. 6,090,503 and in commonly-assigned and co-pending U.S. patent application 2006/0247714, which are both hereby incorporated by reference; one example of these glasses is known as CABAL-12 glass (developed by Sandia National Laboratories). With reference to the table in FIG. 11 of patent application '714 it may be appreciated that many of these glasses have a relatively high boron oxide content. The boron oxide in these glasses can provide resistance to corrosion by lithium (relevant to battery feedthrough assemblies), and can enhance a reliability of seals created with titanium, for example, used for either or both of feedthrough pins and ferrules. However, the relatively high boron content makes the glasses hygroscopic, so that performance of these types of glasses as a feedthrough insulator in an aqueous environment, for example, as implanted in a human body, has been placed under scrutiny.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIGS. 2A-B are top plan views of two feedthrough assembly configurations.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1A:
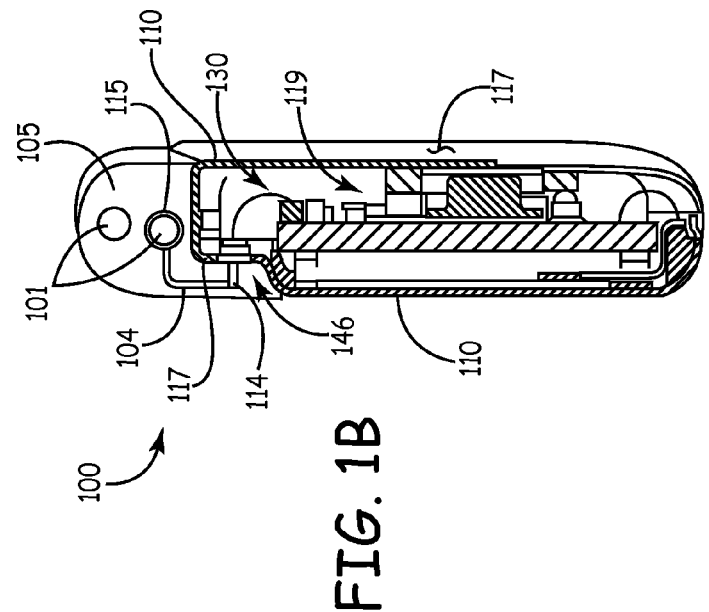
FIG. 1A is a plan view, including a partial section, of an implantable medical device, which may incorporate embodiments of the present invention.

FIG. 1A is a plan view, including a partial section, of an implantable medical device 10, which may incorporate embodiments of the present invention. FIG. 1A illustrates device 10 including a housing sidewall 11, which encloses an interior portion 13 thereof, and a feedthrough assembly 46 for electrically coupling electronic circuitry 19, which is contained within inner portion 13, to an external component 18 of device 10, for example, an electrode. FIG. 1A further illustrates feedthrough assembly 46 including a ferrule 12, which is mounted to housing sidewall 11, for example, via a weld, a feedthrough pin 14 and an insulator 16, which surrounds pin 14 within ferrule 12 and is hermetically sealed to pin 14 and ferrule 12; ferrule 12 and pin 14 are shown extending between an exterior surface 17 of housing sidewall 11 and interior portion 13. Ferrule 12 and housing sidewall 11 may be formed from Titanium (Ti) and pin 14 may be formed from Niobium (Nb).

According to some embodiments of the present invention, which will be described in greater detail below, insulator 16 is glass of a CABAL-12 type composition, and a surface of insulator 16, which faces toward external component 18, is exposed to phosphate-containing body fluids, when device 10 is implanted. CABAL-12 glass consists primarily of aluminum oxide ($Al_2O_3$):boron oxide ($B_2O_3$):calcium oxide (CaO):magnesium oxide (MgO), for example, with relative approximate concentrations of 20:40:20:20 (mol %), and sodium oxide ($Na_2O$), potassium oxide ($K_2O$), silicon oxide ($SiO_2$) and arsenic oxide ($As_2O_3$) at maximum concentrations of thousands parts per million. Approximately 80 mol % of CABAL-12 glass is $B_2O_3$, CaO and MgO, which react with water (pH from ~5 to ~11.5) to form boric acids, calcium hydroxides and magnesium hydroxides, which have fairly good ionic conductivity in the wet environment; thus it may be appreciated that glass of the CABAL-12 type composition could be subject to degradation over time in an aqueous environment, which degradation could compromise feedthrough electrical performance and, potentially, hermetic sealing of device 10. However, when phosphate is present, as is the case for body fluid in an implant environment, for example, either subcutaneous or venous, calcium phosphates are also formed by the reaction, and a layer comprising calcium phosphate, having a relatively low solubility, forms over an exposed surface of the glass; this surface layer comprising calcium phosphate has a protective effect preventing further degradation of the glass insulator. Thus, direct exposure of insulator 16 to body fluids, as opposed to indirect exposure, in which the phosphate content of the body fluid is filtered out (described in greater detail, below), can assure that feedthrough 46 is not compromised, as long as shorting between pin 14 and ferrule 12, via the body fluid, is prevented. Other glasses including CaO in concentrations approximately equal to or greater than CABAL-12 glass, which are known to those skilled in the art, include, without limitation, CVP type, CABAL-17, TIG9 and TIG24.

Figure 1B:
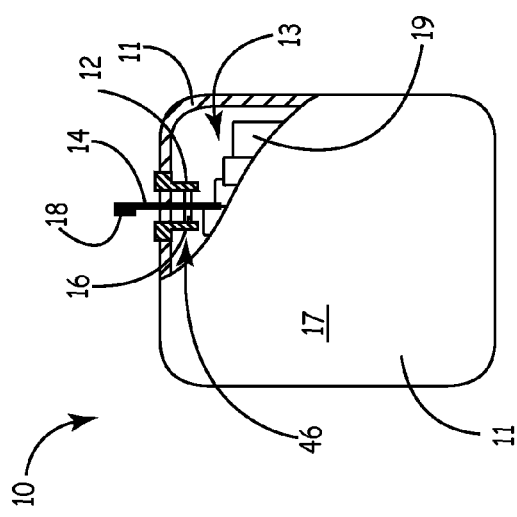
FIG. 1B is a section view of another implantable medical device which may incorporate embodiments of the present invention.
Figure 1C:
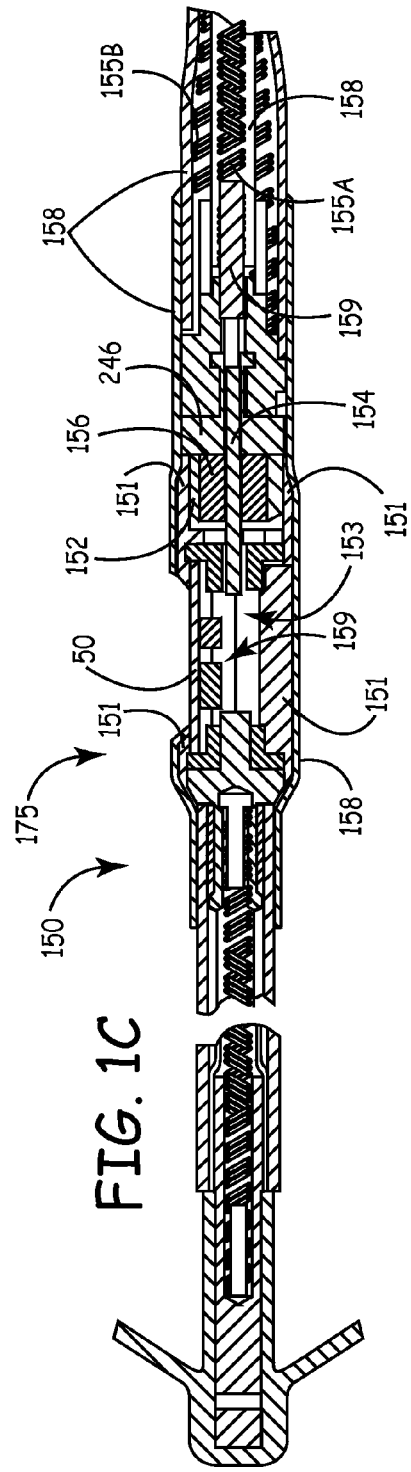
FIG. 1C is a section view of yet another implantable medical device, which may incorporate embodiments of the present invention.

FIGS. 1B-C are section views of other implantable medical devices 100, 150 which may incorporate embodiments of the present invention. FIG. 1B illustrates device 100, like device 10 of FIG. 1A, including a housing sidewall 110, which encloses an interior portion 130 thereof, and a feedthrough assembly 146 for electrically coupling electronic circuitry 119, which is contained within inner portion 130, to an external component 115 of device 100, which, in this case, is a connector contact mounted in a header 105 of device 100. Feedthrough assembly 146 may either be a multipolar-type assembly 200, which is shown in the top plan view of FIG. 2A, or a unipolar-type assembly 20, which is shown in the top plan view of FIG. 2B, or an array of unipolar-type assemblies. FIGS. 2A-B illustrate feedthrough assemblies 200, 20 including a ferrule 201, 21, through which at least one feedthrough pin 114 extends, an insulator 202, 22, preferably glass, which surrounds pin(s) 114, within ferrule 201, 21, and is hermetically sealed to pin(s) 114 and to ferrule 201, 21, and an optional ceramic member 35, 350, for example, formed from sapphire or alumina ($Al_2O_3$), which extends around pin 114 within ferrule 201, 21 and is bonded to glass insulator 202, 22. Those skilled in the art will appreciate that an array of unipolar type assemblies may include a single ferrule having multiple openings, each surrounding individual glass insulators 22 and ceramic members 35, or that an array of assemblies 20 may be mounted in a ferrule flange having multiple openings to which each of ferrules 21 may be welded.

FIG. 1B further illustrates feedthrough pin 114 extending beyond an exterior surface 117 of housing sidewall 110 to a conductor 104, for example, a conductive trace or wire embedded in header 105, which couples connector contact 115 to pin 114. According to the illustrated embodiment, header 105, which is otherwise known as a connector module, is formed from an insulative biostable and biocompatible material, for example, silicone rubber or polyurethane, or a combination thereof, and includes one or more ports 101 for the connection, to device 100, via connector contacts mounted therein, for example, like connector contact 115, of one or more other implantable medical devices, for example, like implantable medical electrical lead 150, which is shown in FIG. 1C.

FIG. 1C illustrates a distal portion of lead 150, in which a pressure sensor assembly 175 is mounted; pressure sensor assembly 175 is shown electrically coupled to coaxially arranged conductors 155A, 155B, which those skilled in the art understand are electrically isolated from one another and extend proximally from sensor assembly 175, within an outer insulation 158 of lead 150 to a proximal end thereof (not shown). At least one connector leg terminates lead 150, at the proximal end thereof, and includes connector contacts, one corresponding to each conductor 155A, 155B, for coupling with corresponding connector contacts, like contact 115 (FIG. 1B), of another device, for example, device 100. Thus, those skilled in the art will appreciate that device 100 and device 150 may function together as an implantable system. Those skilled in the art will further appreciated that device 100, alternatively or in addition, may be connected to an implantable medical electrical lead which includes electrodes for electrical sensing and or delivery of pacing and/or defibrillation pulses, so that electronic circuitry 119 of device may be adapted to support a electrical sensing and pulse generation and/or the sensor function of pressure sensor assembly 175.

FIG. 1C further illustrates pressure sensor assembly 175 including a housing sidewall 151, which encloses an interior portion 153 thereof, and a feedthrough assembly 246 for electrically coupling electronic circuitry 159, which is contained within inner portion 153, to conductor 155A. According to the illustrated embodiment, housing sidewall 151, preferably formed from Ti, supports a deformable pressure-sensitive diaphragm 50, as one plate of a variable pickoff capacitor, and electronic circuitry 159 includes a ceramic hybrid circuit substrate supporting sensing and reference capacitors and a pressure signal modulating circuit, for example, as described in commonly assigned U.S. Pat. No. 5,564,434, pertinent portions of which are hereby incorporated by reference. Feedthrough assembly 246 is shown including a ferrule 152 mounted to sidewall 151, for example, via a weld, a feedthrough pin 154, extending through ferrule 152 from interior portion 153, and an insulator 156 surrounding pin 154 within ferrule 152 and being sealed to pin 154 and to ferrule 152 (similar to unipolar-type assembly 20, FIG. 2B). According to the illustrated embodiment, pin 154 is coupled to a conductive extension 159, which is in turn coupled to conductor 155A, in order to couple conductor 155A to electronic circuitry 159 within interior portion 153 of housing sidewall 151.

With reference to FIGS. 1B-C, it may be appreciated that housing sidewalls 110, 151 and feedthrough assemblies 146, 246 are surrounded, at least in part, by an exterior secondary housing, which is intended to isolate the feedthrough from contact with body fluids of the implant environment; the secondary housing of device 100 is connector module 105, and the secondary housing of device/lead 150 is the outer insulation 151 in conjunction with underlying insulative members. Even while providing effective isolation in several respects, these secondary housings, particularly if formed, at least in part, by silicone rubber, can, over time allow ingress of water; standard medical grade silicone rubbers have been found to filter out ionics present in human body fluid, so that, although the water, which may eventually reach that portion of the feedthrough assembly 146, 246 on the exterior side of housing sidewall 110, 151, will not, itself, form a shorting path between the respective pins and ferrules of the assemblies, the water has the potential to be absorbed by the glass insulators of the assemblies, particularly if the glass insulators are CABAL-12 glass, or another glass of a CABAL-12 type composition; an exposed portion of the glass insulators can thereby react with the water and form a reacted layer, as described above, in conjunction with FIG. 1A. The electrical insulation function of the feedthrough assemblies can be compromised if the reacted layer forms a conductive bridge between the pin and ferrule, and the hermetic sealing function could also be compromised, if the reaction continues. However, if a direct path between the implant environment and the glass insulators of feedthrough assemblies 146, 246 exists in devices 100, 150, the ionics, particularly phosphate, of the body fluid will not be filtered out, thereby allowing a self-limiting reaction that forms a protective surface layer comprising calcium phosphate on the glass insulators, as previously described for device 10 of FIG. 1A. Some embodiments along this line will be described below, in conjunction with FIGS. 6A-B.

Figure 3B:
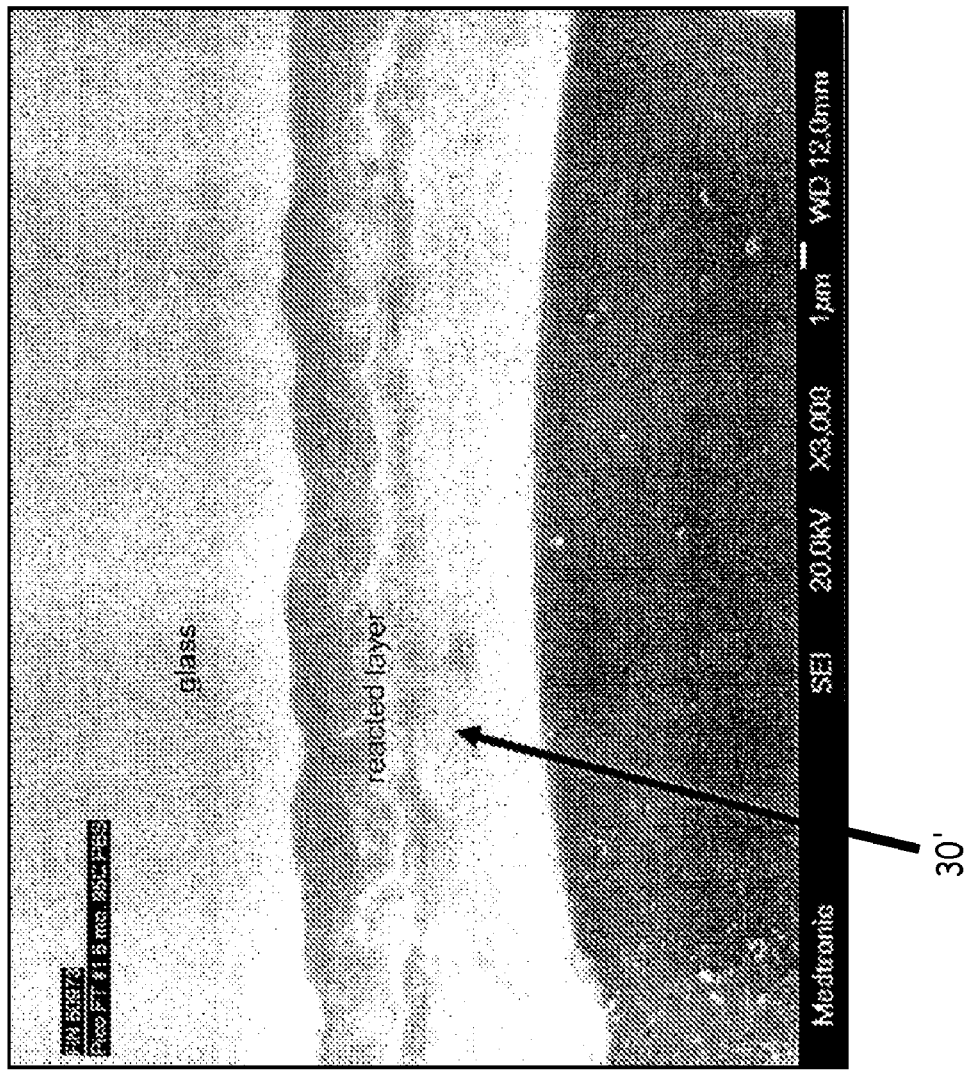
FIG. 3B is a scanning electron microscope (SEM) image of a glass insulator surface layer, according to some embodiments.
Figure 3A:
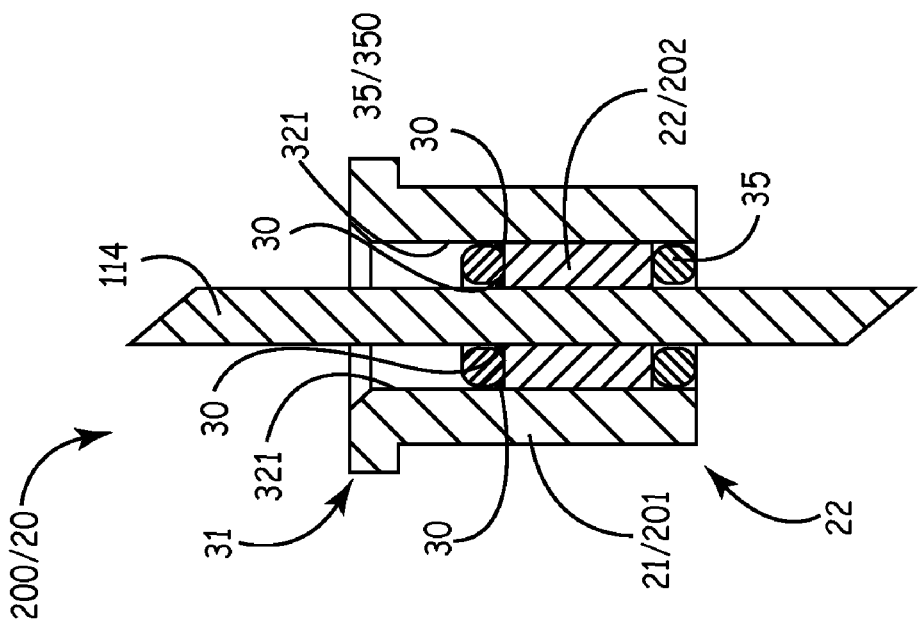
FIG. 3A is a section view, through section line A-A of FIGS. 2A-B, of a feedthrough configuration, according to some embodiments of the present invention.

According to a group of alternate embodiments, feedthrough assemblies, for example, either multipolar-type 200 or unipolar-type 20, or an array of unipolar-types, include insulators that are formed with CABAL-12 glass, or any other glass of the CABAL-12 type composition, and that are pre-treated to form the surface layer comprising calcium phosphate. FIG. 3A is a section view, through section line A-A of FIGS. 2A-B, of feedthrough assembly 20/200 including glass insulator 22/202, which has been pre-treated to include a layer 30, which layer 30 comprises calcium phosphate, according to some embodiments of the present invention; and FIG. 3B is a SEM image of an exemplary surface layer 30', which comprises calcium phosphate and has been formed over a sample feedthrough assembly including a CABAL-12 glass insulator. It should be noted that either multipolar-type feedthrough assembly 200 or unipolar-type feedthrough assembly 20, as depicted in FIG. 3A, may be incorporated into either of devices 10, 100 as assembly 46, 146, respectively (FIGS. 1A-B), and unipolar-type assembly 20 into device 150 as assembly 246 (FIG. 1C).

FIG. 3A illustrates ferrule 21/201 of feedthrough assembly 20/200 extending from a first end 31 to a second end 32 thereof, and surface layer 30 located on both sides of the interface with ceramic member 35/350, one between pin 114 and member 35/350 and another between ferrule 21/201 and member 35/350, on a side of insulator 22/202 that corresponds to first end 31 of ferrule 21/201, which end 31 would be adjacent to an exterior surface of a housing sidewall, for example, either of surfaces 17, 117 of respective sidewall 11, 110 (FIGS. 1A-B). FIG. 3A further illustrates feedthrough assembly 20/200 including another ceramic member 45 surrounding pin 114 within ferrule 21/201 and located adjacent to a side of insulator 22/202 that is opposite surface layer 30, in proximity to second end 32 of ferrule 21/201. According to the illustrated embodiment, ceramic member 45, for example, formed from sapphire or alumina ($Al_2O_3$), is optionally included to prevent glass insulator 22/202 from adhering to a fixture within ferrule 21/201 during the heating process in which insulator 22/202 is sealed to ferrule 21/201 and pin 114; during that process, both ceramic members 35/350, 45 are bonded to the adjacent surface of insulator 22/202. Hermetically sealing of CABAL-12 type glass insulators to Ti ferrules and to Nb pins is typically accomplished at a temperature in a range from approximately 790° C. to approximately 810° C., for a time in a range from approximately 3 minutes to approximately 4 minutes. Those skilled in the art will appreciate that ceramic member 35/350 can provide added protection to glass insulator, thereby improving a longevity of feedthroughs.

A barrier to prevent shorting between pin 114 and ferrule 21/201, via the body fluid, may be necessary, even though surface layer 30 and ceramic member 35/350 protect glass insulator 22/202 from degradation, if and when a protective layer of a device, in which feedthrough assembly 20/200 is included, for example, the secondary housing previously described in conjunction with FIGS. 1A-B, becomes breached, or otherwise allows body fluids to come into contact with insulator 22/202. FIG. 3A illustrates ferrule 21/201 further including an insulative coating 321, for example, aluminum oxide $Al_2O_3$, formed, for example, by atomic layer deposition (ALD), along an inner surface thereof, to prevent shorting between ferrule 21/201 and pin 114. Alternately, or in addition, an area between pin 114 and ferrule 21/201, over surface layer 30 and ceramic member 35/350, may be potted, or backfilled with an insulative material, for example, silicone adhesive, as shown by the speckling in FIG. 3A. Another means to prevent the shorting will be described below, in conjunction with FIG. 5A.

Turning now to FIG. 3B, an actual surface layer 30', which comprises calcium phosphate, of a glass insulator of a sample feedthrough assembly is shown at 3,000× magnification in the SEM image (secondary mode). The sample feedthrough assembly is one of a group of samples which were assembled for environmental testing, which testing was designed to accelerate the degradation of CABAL-12 type glass in an aqueous environment. Each sample was constructed in unipolar form (FIG. 2B) as shown in FIG. 3A, using CABAL-12 glass for insulator 22/202 (glass composition previously described, in conjunction with FIG. 1), Nb, for pin 114, Ti, for ferrule 21/201, and sapphire discs for ceramic members 35, 45. A maximum outer diameter of the ferrule of each sample was approximately 0.038 inch and an inner diameter of the ferrule of each sample was approximately 0.023 inch. Samples were immersed in a corresponding volume of phosphate buffered saline (PBS), which had a total chloride concentration of approximately 0.140M and a phosphate concentration of approximately 0.010M, and each sample was subjected to open circuit conditions and a temperature of approximately 95° C. The volume of the PBS in which each assembly was immersed was such that a ratio of exposed glass surface area to volume of solution was approximately 0.011 $cm^{-1}$.

The SEM image of FIG. 3B was generated after the corresponding sample had been immersed in the PBS for six months. A thickness of layer 30' is on the order of 0.001 inch and, for some other samples of the group, that were kept immersed in the PBS, at the above-described conditions, for at least twelve months, the thickness of the surface layer, which comprised calcium phosphate, and was formed over the glass insulator of each, was found to be approximately the same as that for the sample shown in the SEM image. For yet other samples of the group, a surface layer, which comprised calcium phosphate and had a thickness of less than approximately 0.001 inch, was observed between one and six months of immersion in the PBS, at the above-described conditions. It should be noted that the layer formed only on the exposed portions of the glass surface and not underneath the sapphire disc (i.e. ceramic member 35/350, FIG. 3A). In addition to the visual observations of the surfaces of the glass insulator of each sample, an impedance of each sample was evaluated via electrochemical impedance spectroscopy measurements and no reduction in impedance was observed after twelve months for any of the samples.

Figure 4:
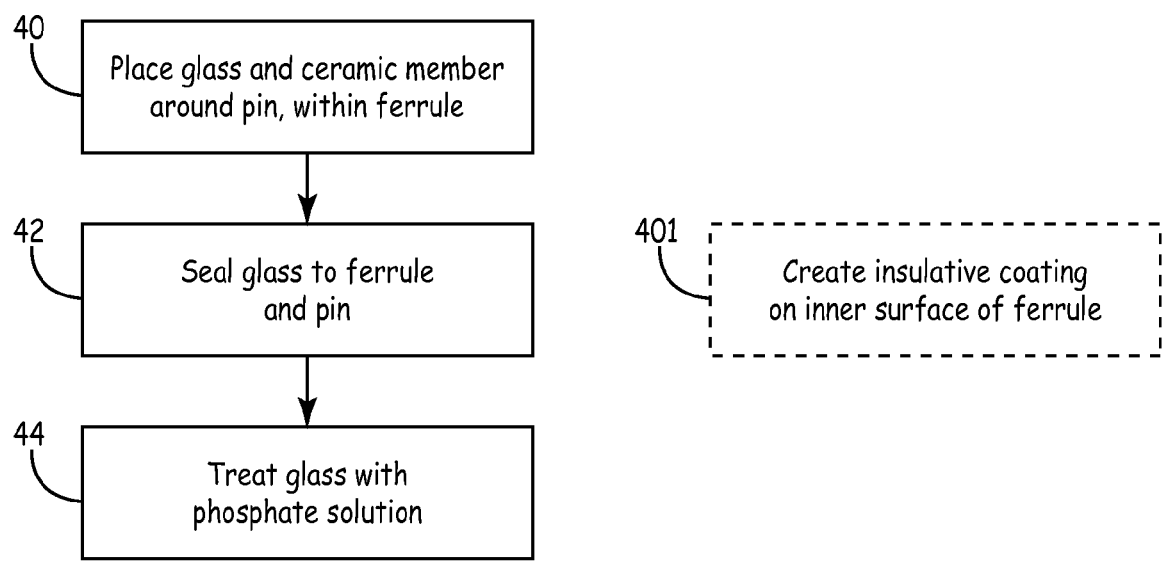
FIG. 4 is a flow chart outlining some methods of the present invention.

In light of the above results, a pre-treatment of feedthrough assemblies, which include CABAL-12 type glass insulators, in order to form the surface layer that comprises calcium phosphate, is contemplated, as previously described in conjunction with FIG. 3A. With reference to FIG. 4, several methods for manufacturing a feedthrough assembly, according to some embodiments of the present invention, will now be outlined. FIG. 4 illustrates a step 40, in which the glass insulator and ceramic member(s) are placed about the pin, within the ferrule, and a subsequent step 42 in which the glass insulator is sealed to the ferrule and pin of the feedthrough assembly. It should be noted that either one or a pair of ceramic members may be included in the assembly and that, during step 42, the ceramic member(s) is/are bonded to the glass insulator. Following steps 40 and 42, the glass insulator is treated with a phosphate solution to form, per step 44, a surface layer comprising calcium phosphate, over that surface of the glass insulator that will potentially be exposed to body fluids, for example, the surface corresponding to first end 31 of ferrule 21/201 (FIG. 3A). According to some exemplary methods of the present invention, step 44 is carried out by immersing at least that portion of the sealed assemblies, which include this surface of the glass insulator, in a solution of approximately 0.01 M phosphate $PO_4^{3-}$, that has a pH of approximately 7.4 (at room temperature), at a temperature between approximately 50° C. and approximately 95° C., for a time between approximately 1 day and 7 days.

Figure 5A:
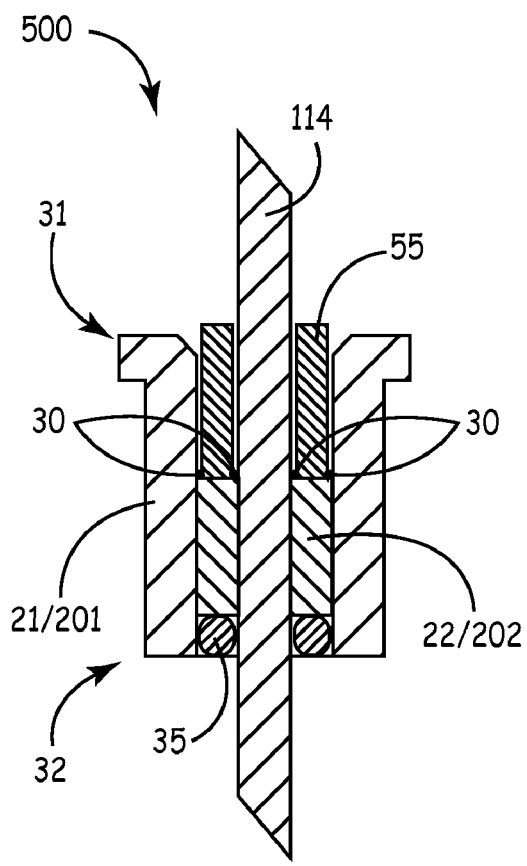
FIGS. 5A-B are a section views of feedthrough assemblies, according to some alternate embodiments of the present invention.
Figure 5B:
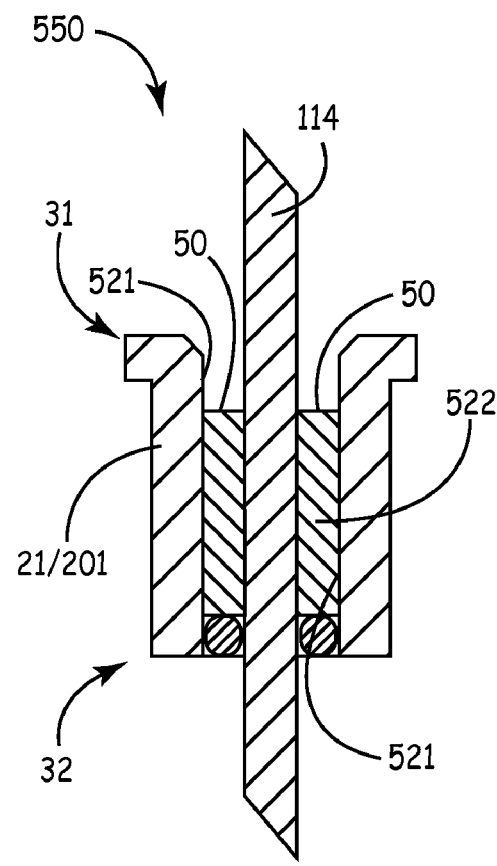

FIG. 4 further illustrates an optional step 401, which may either precede step 40, or follow step 42, either prior to, or following step 44. According to step 401, an insulative coating, for example, alumina, is formed along an inner surface of the ferrule, for example, by ALD, to prevent shorting between the ferrule and pin, as previously described (coating 321, FIG. 3A). Turning now to FIG. 5A, a feedthrough assembly 500 is shown including a ceramic member 55, which is bonded to the surface of glass insulator 22/202 and extends beyond first end 31 of ferrule 21/201 in order to provide a shorting barrier such that the aforementioned insulative coating is not necessary. However, if such an insulative coating is formed, then the assembly need not include either ceramic member 35/350 of FIG. 3A, nor ceramic member 55 of FIG. 5A, and step 40 (FIG. 4) need not include the placement of that ceramic member. FIG. 5B illustrates an assembly 550 according to such an embodiment, wherein a surface layer 50, which comprises calcium phosphate, is shown extending over the entire surface of a glass insulator 522, for example, formed from a glass having a CABAL-12 type composition. According to the illustrated embodiment, an insulative layer 521, for example, alumina, extends along the inner surface of ferrule 21/201 from first end 31 of ferrule 21/201 to second end 32 of ferrule 21/201, having been formed, for example, according to step 401 of FIG. 4, prior to step 40.

Figure 6A:
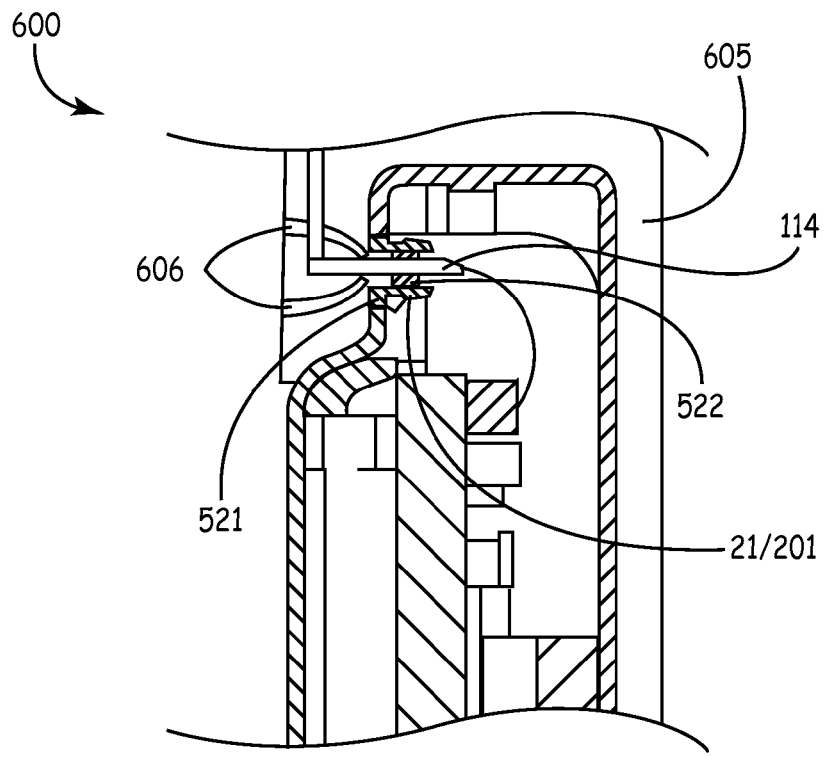
FIGS. 6A-B are section views of portions of a pulse generator implantable device and a pressure sensor implantable device, respectively, according to some embodiments.
Figure 6B:
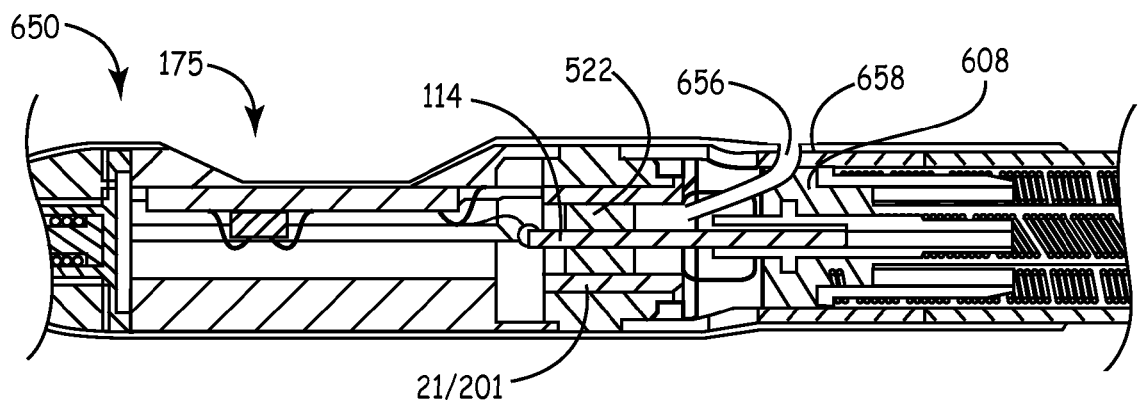

With further reference to FIG. 5B, it should be noted that, according to alternate embodiments, glass insulator 21/201 may be positioned such that surface layer 50 is approximately flush with first end 31 of ferrule 21/201 or protrudes above first end 31. According to yet further embodiments of the present invention, step 44 may be omitted from the method for manufacturing assembly 550 and surface layer 50 may be formed after assembly 550 is incorporated within an implantable device and the device has been implanted, as previously described. FIGS. 6A-B present examples of such embodiments.

FIGS. 6A-B are section views of portions of a pulse generator implantable device 600 and a pressure sensor implantable device 650, respectively, each including feedthrough assembly configuration similar to that of assembly 550 shown in FIG. 5B, according to some embodiments, wherein exposure of glass insulator 522 to phosphate-containing body fluid, when devices 600, 650 are implanted, produces surface layer 50. FIG. 6A illustrates a header, or connector module 605 of device 600 including channels 606 formed therein to allow passage therethrough of phosphate-containing body fluids from the implant environment for direct contact with insulator 522. FIG. 6B illustrates an outer insulation 658 and an underlying insulative member 608 of device 650 having a channel 656 formed therein to allow passage therethrough of phosphate-containing body fluids from the implant environment for direct contact with insulator 522. It should be noted that either or both feedthrough assemblies of devices 600, 650 may alternately be configured to include either ceramic member 35/350, as shown in FIG. 3A, or ceramic member 55, as shown in FIG. 5A.

In the foregoing detailed description, the invention has been described with reference to specific embodiments. However, it may be appreciated that various modifications and changes can be made without departing from the scope of the invention as set forth in the appended claims.

We claim:

1. An implantable medical device comprising:
   electronic circuitry;
   a housing including a sidewall enclosing an interior portion of the housing, which interior portion contains the electronic circuitry, the sidewall including an exterior surface;
   a feedthrough assembly, the assembly comprising:
      a ferrule mounted to the sidewall of the housing and extending from a first end of the ferrule to a second end of the ferrule, the first end being adjacent to the exterior surface of the housing sidewall;
      a pin coupled to the electronic circuitry within the housing and extending through the ferrule between the first and second ends thereof; and
      a glass insulator containing at least approximately 20 mol % of CaO, the glass insulator surrounding the pin, within the ferrule, and being sealed to the pin and to the ferrule, the glass insulator including a surface, which is located on a side of the glass insulator that corresponds to the first end of the ferrule;
      wherein at least a portion of the surface of the glass insulator is exposed for contact with phosphate-containing body fluid when the device is implanted; and
   a second housing surrounding at least that portion of the sidewall where the ferrule of the feedthrough assembly is mounted and surrounding at least a portion of the feedthrough assembly at the exterior surface of the sidewall;
      wherein the second housing includes a channel extending from an opening of the channel to the feedthrough assembly, the channel opening being located at an exterior surface of the second housing, and the channel allowing the surface of the glass insulator to be exposed for contact with the body fluid when the device is implanted.

2. The device of claim 1, wherein the feedthrough assembly further comprises a ceramic member extending around the pin and within the ferrule, the ceramic member being bonded to the glass insulator and located between the glass insulator and the first end of the ferrule.

3. The device of claim 2, wherein the ceramic member further extends beyond the first end of the ferrule.

4. The device of claim 1, wherein the ferrule of the feedthrough assembly includes an insulating layer extending over an inner surface of the ferrule, which inner surface faces the pin, the insulating layer extending at least from beneath the surface of the glass insulator to the first end of the ferrule.

5. The device of claim 1, wherein the feedthrough assembly further comprises a ceramic member extending around the pin and within the ferrule, the ceramic member being bonded to the glass insulator and located between the glass insulator and the first end of the ferrule.

6. The device of claim 5, wherein the ceramic member further extends beyond the first end of the ferrule.

7. The device of claim 1, wherein the ferrule of the feedthrough assembly includes an insulating layer extending over an inner surface of the ferrule, which inner surface faces the pin, the insulating layer extending at least from beneath the surface of the glass insulator to the first end of the ferrule.

8. The device of claim 1, wherein the electronic circuitry supports a pulse generator function of the device.

9. The device of claim 1, wherein the electronic circuitry supports a sensor function of the device.

* * * * *